United States Patent [19]

Sasa

[11] Patent Number: 4,637,378
[45] Date of Patent: Jan. 20, 1987

[54] CLEANING APPARATUS FOR ENDOSCOPE

[75] Inventor: Hiroyuki Sasa, Tokyo, Japan

[73] Assignee: Olympus Optical Co., Ltd., Tokyo, Japan

[21] Appl. No.: 792,492

[22] Filed: Oct. 28, 1985

[30] Foreign Application Priority Data

Nov. 1, 1984 [JP] Japan .................. 59-230667
Nov. 22, 1984 [JP] Japan .................. 59-247416

[51] Int. Cl.$^4$ .......................... A61B 1/12; B08B 9/02
[52] U.S. Cl. ........................................ 128/4; 134/102;
134/166 C; 134/168 C
[58] Field of Search .................... 128/4, 6; 134/166 C, 134/102, 168 C

[56] References Cited

U.S. PATENT DOCUMENTS

| 3,963,438 | 6/1976 | Banez | 128/6 X |
| 4,325,362 | 4/1982 | Ouchi et al. | 128/4 |
| 4,509,507 | 4/1985 | Yabe | 128/4 |
| 4,537,209 | 8/1985 | Sasa | 128/4 X |

FOREIGN PATENT DOCUMENTS

| 0055394 | 7/1982 | European Pat. Off. | 128/4 |
| 0071058 | 2/1983 | European Pat. Off. | 128/4 |
| 0106310 | 4/1984 | European Pat. Off. | 128/4 |
| 3334999 | 4/1985 | Fed. Rep. of Germany | 128/4 |

Primary Examiner—William H. Grieb

[57] ABSTRACT

A cleaning apparatus includes a liquid feeding unit, a connector detachably connected to an endoscope and a connecting unit for guiding a detergent solution fed from the feeding unit to the connector. The connector has a support plate, an air/liquid mouthpiece and a suction mouthpiece which are movably supported by the plate, and a slider supported by the plate to be movable between first and second positions. The mouthpiece has a ring-member which engages with a frange of an air/liquid cylinder of the endoscope. The mouthpiece has a ring-member engaging with a frange of a suction cylinder of the endoscope. When the slider is moved to the second position, a first holding portion and a second holding portion thereof hold the franges, in cooperation with the ring-members, by using an urging force or urging members.

19 Claims, 31 Drawing Figures

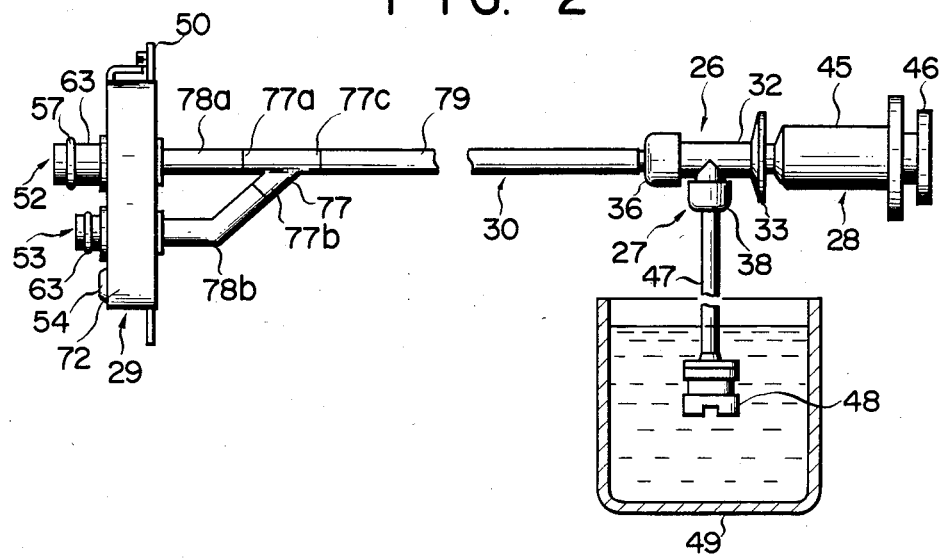
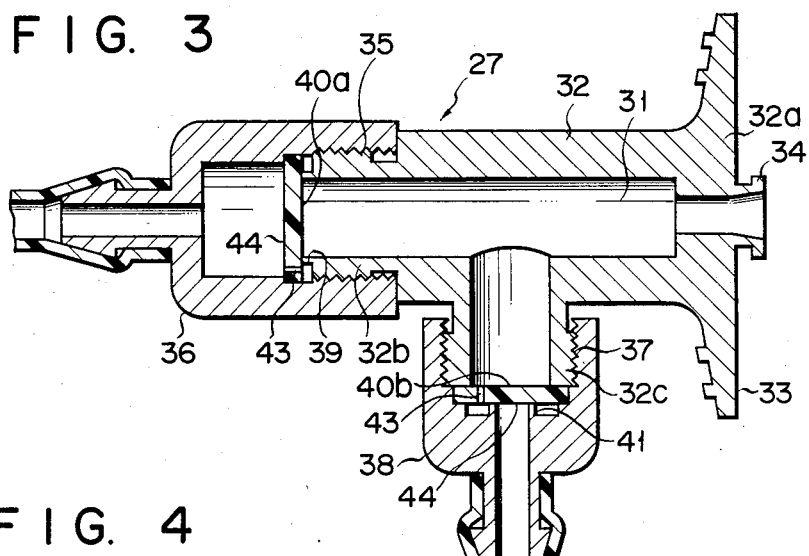
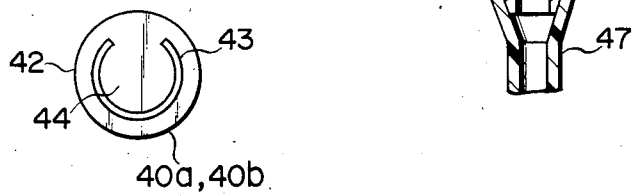

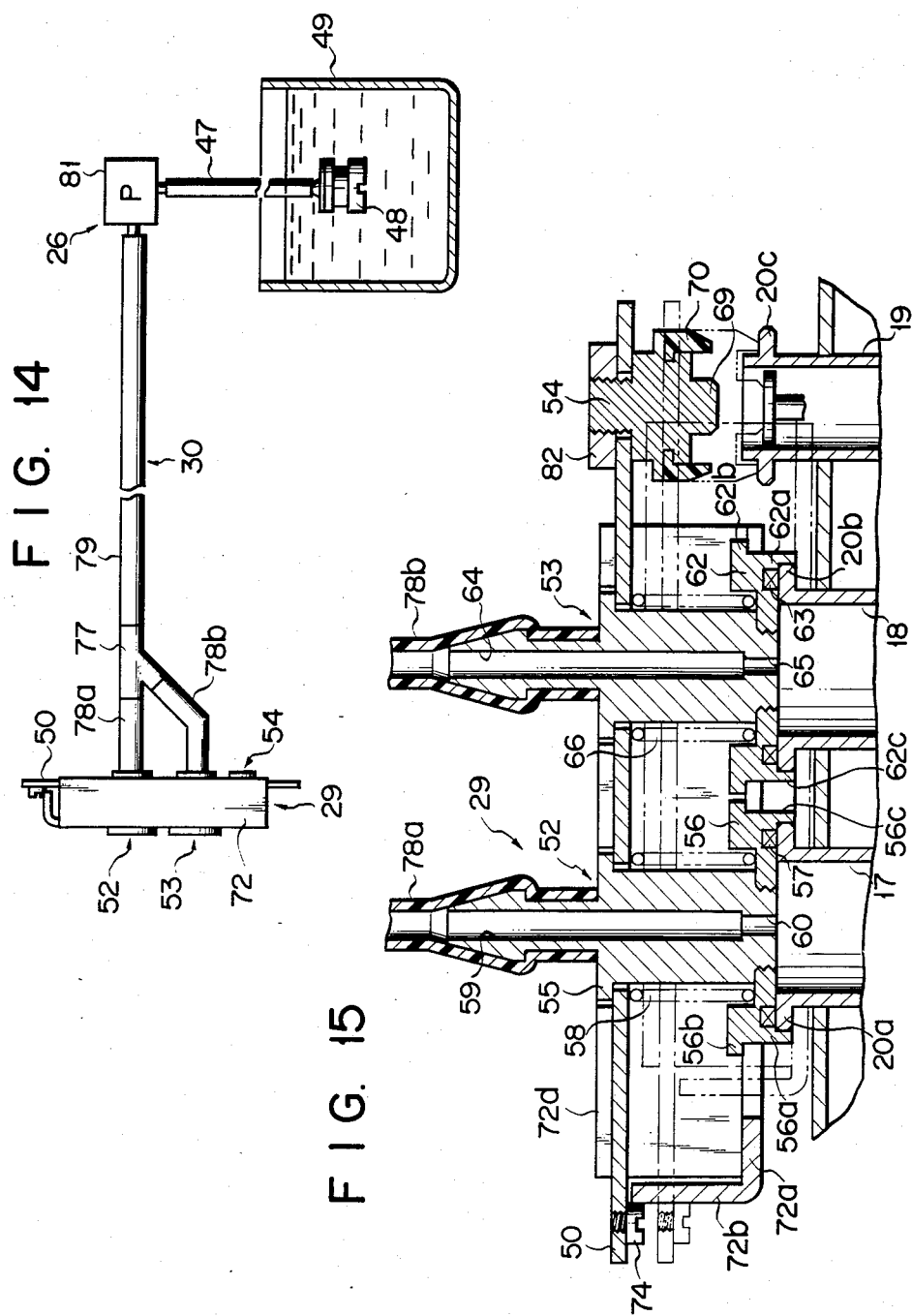

F I G. 24A
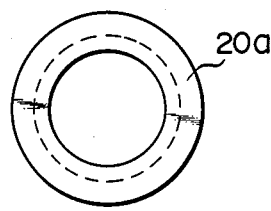
F I G. 25A
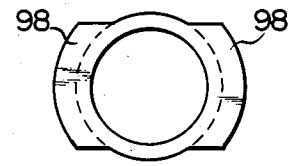
F I G. 24B
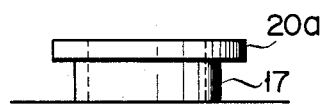
F I G. 25B
F I G. 26A
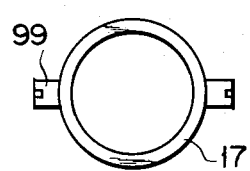
F I G. 27A
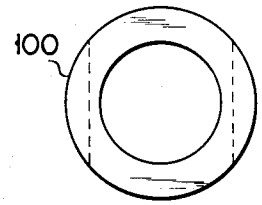
F I G. 26B
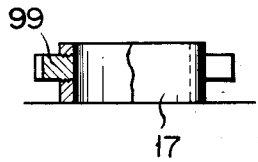
F I G. 27B
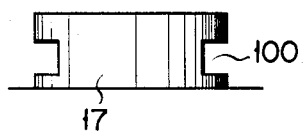

CLEANING APPARATUS FOR ENDOSCOPE

BACKGROUND OF THE INVENTION

The present invention relates to a cleaning apparatus for cleaning the inside of channels of an endoscope.

In general, an endoscope is provided with a plurality of channels for air feed, liquid feed, suction, etc. An operating section of the endoscope includes a plurality of cylinders which communicate with the channels. A piston for opening and closing the channel is inserted in each cylinder, constituting a control valve. In a conventional method of channel cleaning, the pistons are removed from their corresponding cylinders, and connectors attached to liquid feed tubes for cleaning are connected to the cylinders so that a detergent solution is fed into the channels through the tubes and the connectors.

Connectors of conventional types include ones which are screwed into a threaded portion formed on the inner peripheral surface of the cylinder and ones which hold a flange formed on the cylinder and are screwed to the flange. It is troublesome, however, to connect to or disconnect these connectors from the cylinder, especially when using a plurality of cylinders.

SUMMARY OF THE INVENTION

The present invention is contrived in consideration of these circumstances, and is intended to provide a cleaning apparatus capable of being easily and securely connected to and disconnected from an endoscope.

In order to achieve the above object, a cleaning apparatus of the present invention comprises liquid feeding means for feeding a detergent solution; a connector detachably connected to an air/liquid cylinder and a suction cylinder of an endoscope; and connecting means for connecting the liquid feeding means and the connector so that the detergent solution fed from the liquid feeding means is delivered into several channels of the endoscope through the connector; the connector including a support body, an air/liquid mouthpiece movably supported by the support body and connected to an open end portion of the air/liquid cylinder in a liquid-tight manner, the air/liquid mouthpiece having a liquid passage communicating with the inside of the air/liquid cylinder and the connecting means and a retaining portion engaging an engaging portion of the open end portion of the air/liquid cylinder, a suction mouthpiece movably supported by the support body and connected to an open end portion of the suction cylinder in a liquid-tight manner, the suction mouthpiece having a liquid passage communicating with the inside of the suction cylinder and the connecting means and a retaining portion engaging an engaging portion of the open end portion of the suction cylinder, a slider slidably supported by the support body and having a first holding portion adapted to engage the engaging portion of the air/liquid cylinder and a second holding portion adapted to engage the engaging portion of the suction cylinder, the slider being movable between a first position where the first and second holding portions of the slider are disengaged from the engaging portions of the cylinders, and a second position where the first holding portion engages the engaging portion of the air/liquid cylinder so that the engaging portion of the air/liquid cylinder is held between the first holding portion and the retaining portion of the air/liquid mouthpiece, and where the second holding portion engages the engaging portion of the suction cylinder so that the engaging portion of the suction cylinder is held between the second holding portion and the retaining portion of the suction mouthpiece, and urging means for urging the first and second holding portions toward the respective retaining portions of the air/liquid mouthpiece and the suction mouthpiece when the slider is moved to the second position.

BRIEF DESCRIPTION OF THE DRAWINGS

FIGS. 2 to 11 show a cleaning apparatus according to a first embodiment of the present invention, in which FIG. 2 is a side view showing an outline of the apparatus, FIG. 3 is a sectional view of a simple-frame pump, FIG. 4 is a side view of a check valve, FIG. 5 is a sectional view of a connector, FIG. 6 is a top view of the connector, FIG. 7 is a bottom view of the connector, FIG. 8 is a sectional view taken along line VIII—VIII of FIG. 5, FIGS. 9 and 10 are a sectional view and a bottom view, respectively, of the connector in a state different from the one shown in FIG. 5, and FIG. 11 is a sectional view taken along line XI—XI of FIG. 9;

FIGS. 12 and 13 show a modification of the first embodiment, in which

FIG. 12 is a sectional view of a branch pipe, and

FIG. 13 is a side view showing an outline of the apparatus;

FIGS. 14 to 17 show a cleaning apparatus according to a second embodiment of the invention, in which FIG. 14 is a side view showing an outline of the apparatus, FIG. 15 is a sectional view of a connector, FIG. 16 is a top view of the connector, and FIG. 17 is a side view of the endoscope;

FIGS. 24A and 24B are a plan view and a side view, respectively, showing a first modified example of an engaging portion of a cylinder;

FIGS. 25A and 25B are a plan view and a side view, respectively, showing a second modified example of the engaging portion of the cylinder;

FIGS. 26A and 26B are a plan view and a side view, respectively, showing a third modified example of the engaging portion of the cylinder; and FIGS. 27A and 27B are a plan view and a side view, respectively, showing a fourth modified example of the engaging portion of the cylinder.

DETAILED DESCRIPTION OF THE PREFERRED EMBODIMENTS

Preferred embodiments of the present invention will now be described in detail with reference to the accompanying drawings.

Figure 1:
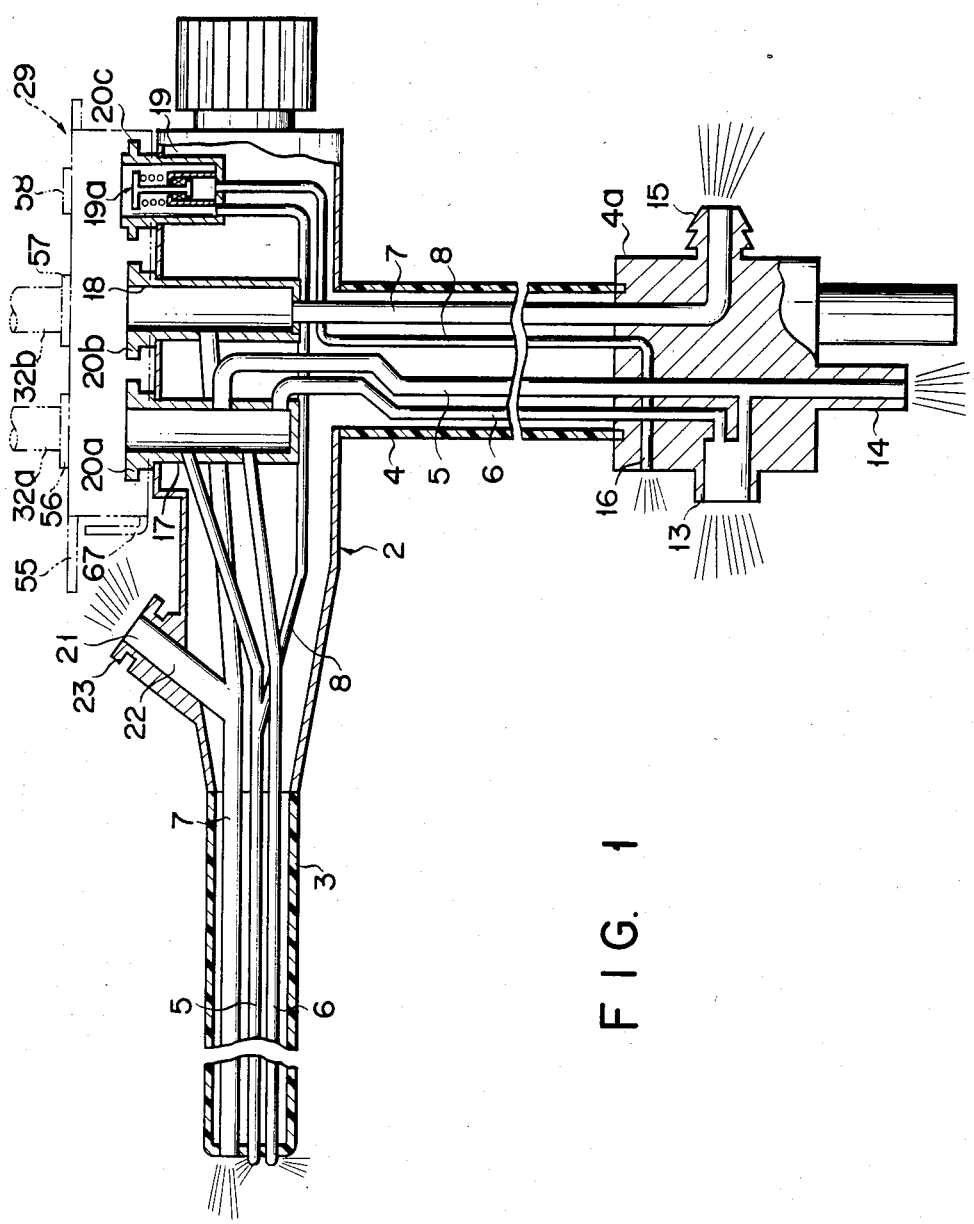
FIG. 1 is a sectional view of an endoscope.

FIG. 1 shows a conventional endoscope. The endoscope comprises an operating section 2, an insertion section 3 extending from the operating section, and a universal cord 4 extending from the operating section and having a connector 4a at its distal end. Inside the endoscope, an air channel 5, a liquid channel 6, a suction channel 7, and a gas channel 8 extend through the insertion section 3, the operating section 2, and the universal cord 4. The air channel 5, the liquid channel 6, and the gas channel 8 are narrower and smaller in capacity than the suction channel 7. The air, liquid and suction channels 5, 6 and 7 open at one end to the distal end face of the insertion section 3. The other end of the air channel 5 opens into a liquid mouthpiece 13 and an air mouthpiece 14 formed on the connector 4a. The other end of the liquid channel 6 opens into the liquid mouthpiece 13 of the connector 4a, and that of the suction channel 7 into a suction mouthpiece 14 formed on the connector 4a. One end of the gas channel 8 communicates with the air channel 5, while the other end thereof opens into a gas mouthpiece 16 formed on the connector 4a.

Disposed in the operating section 2 are an air/liquid cylinder 17 connecting with the middle portions of the air channel 5 and the liquid channel 6, a suction cylinder 18 connecting with the middle portion of the suction channel 7, and a gas cylinder 19 connecting with the middle portion of the gas channel 8. The cylinders 17, 18 and 19 are arranged at regular intervals in a line in the operating section 2. The upper end portion of the air/liquid cylinder 17 projects from the operating section 2, and is formed with a flange 20a as an engaging portion on its outer periphery. Likewise, the upper end portions of the suction cylinder 18 and the gas cylinder 19 project from the operating section 2, and are formed with flanges 20b and 20c as engaging portions, respectively, on their outer periphery.

Normally, an air/liquid piston (not shown) is inserted in the air/liquid cylinder 17, whereby the air channel 5 and the liquid channel 6 are opened and closed, while a suction piston (not shown) for opening and closing the suction channel 7 is inserted in the suction cylinder 18. The gas cylinder 19 has a valve mechanism 19a built-in and normally is fitted with an operating button (not shown) for operating the valve mechanism 19a. The operating section 2 is formed with a forceps mouthpiece 21 having a flange 23 and communicating with the middle portion of the suction channel 7 by means of a forceps channel 22. Thus, a forceps or other medical instrument may be inserted into the suction channel 7 through the forceps mounthpiece 21.

There will now be described a cleaning apparatus for cleaning the channels of the endoscope according to the present invention.

As shown in FIGS. 2 to 4, the cleaning apparatus comprises a liquid feeder 26 for feeding a detergent solution, a connector 29 detachably connected to the cylinders of the endoscope, and a connecting unit 30 connecting the liquid feeder 26 and the connector 29.

The liquid feeder 26 includes a simple-frame pump 27, an injector-shaped operating member 28 for operating the pump 27, and a tank 49 storing a detergent solution. The simple-frame pump 27 is provided with a T-shaped syringe connector 32 having a T-shaped liquid passage 31. The connector 32 has a connecting port portion 32a, an outlet port portion 32b, and an inlet port portion 32c each communicating with the liquid passage 31. A ring-shaped hub 33 and a syringe socket 34 are formed on the outer periphery of the connecting port portion 32a. The outlet port portion 32b is formed with a threaded portion 35 on which an outlet mouthpiece 36 is screwed. Likewise, the inlet port portion 32c is formed with a threaded portion 37 on which an inlet mouthpiece 38 is screwed. A valve seat 39 is formed on the end face of the outlet port portion 32b, and a check valve 40a is interposed between the valve seat 39 and the outlet mouthpiece 36. A valve seat 41 is formed on the suction mouthpiece 38, and a check valve 40b is interposed between the valve seat 41 and the end face of the inlet port portion 32c. As shown in FIG. 4, the check valves 40a and 40b each includes a substantially circular valve 44 which is formed by cutting a substantially horseshoe-shaped slit 43 in a disk member 42 made of an elastic material such as silicone rubber. The respective valves 44 of the check valves 40a and 40b are in contact with their corresponding valve seats 39 and 41.

The operating member 28 consists of a syringe 45 and a piston 46 inserted therein. The distal end of the syringe 45 is connected to the syringe socket 34 of the syringe connector 27. A suction tube 47 is connected at one end to the suction mouthpiece 38, and at the other end to a filter 48 which is immersed in the detergent solution in the tank 49.

Thus, when the piston 46 of the operating member 28 is pulled, the check valve 40b is opened to allow the detergent solution in the tank 49 to be sucked into the liquid passage 31 through the section tube 47. In this state, when the piston 46 is pushed in, the check valve 40a is opened to cause the detergent solution in the liquid passage 31 to be discharged from the outlet mouthpiece 36.

Referring now to FIGS. 5 to 8, the connector 29 will be described in detail.

The connector 29 includes a rectangular support plate 50 made of metal or synthetic resin. The support plate 50 is formed with three apertures 51a, 51b and 51c which are arranged in a line so that their centers are located on the longitudinal center line of the support plate 50. These apertures are spaced at regular intervals equal to those between the air/liquid cylinder 17, the suction cylinder 18, and the gas cylinder 19 on the operating section 2 of the endoscope. The aperture 51a is penetrated by a substantially cylindrical air/liquid injection mouthpiece 52 which is a little shorter in diameter than the aperture 51a and movable in a direction perpendicular to the support plate 50. Likewise, the aperture 51b is penetrated by a substantially cylindrical suction injection mouthpiece 53 which is a little shorter in diameter than the aperture 51b and movable in the direction perpendicular to the support plate 50, and the aperture 51c is penetrated by a substantially cylindrical gas cylinder plug 54 which is a little shorter in diameter than the aperture 51c and movable in the direction perpendicular to the support plate 50.

Figure 5:
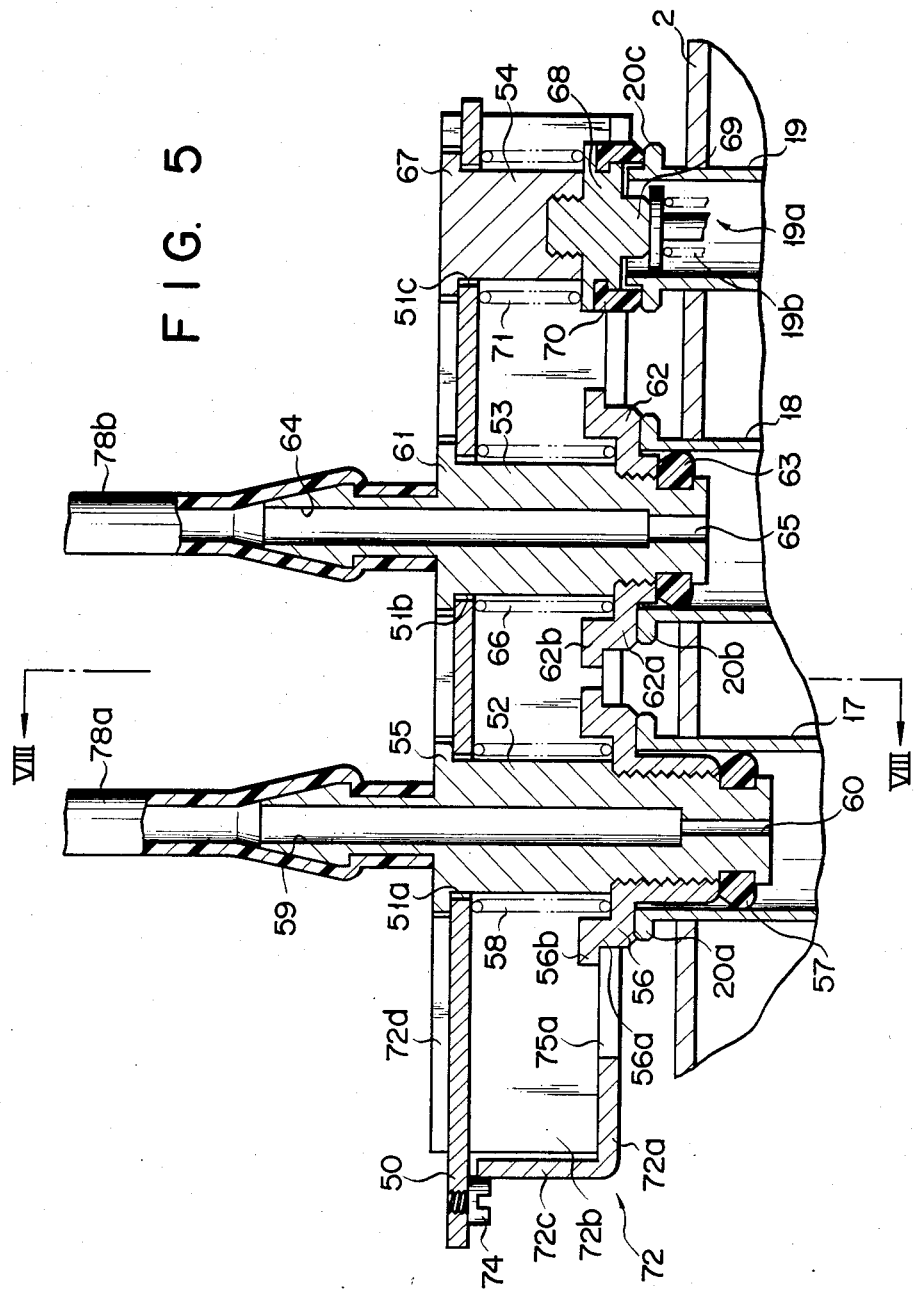

As shown in FIG. 5, a flange 55 is formed on the outer periphery of the upper end portion of the air/liquid injection mouthpiece 52 so as to be located on the upper surface side of the support plate 50. On the lower surface side of the support plate 50, a ring-member 56 as a retaining member is fixed to the outer periphery of the lower end portion of the mouthpiece 52. The ring-member 56 includes a support portion 56a substantially equal in diameter to the flange 20a of the air/liquid cylinder 17 and a collar portion 56b larger in diameter than the support portion 56a. A ring-shaped seal member 57 is fixed on the outer peripheral surface of the mouthpiece 52, underlying the member 56. The lower end portion of the air/liquid injection mouthpiece 52 can be inserted into the air/liquid cylinder 17, with the seal member 57 in air- and liquid-tight contact with the inner peripheral surface of the cylinder 17. A compression spring 58 as a first urging member is interposed between the support plate 50 and the ring-member 56, whereby the mouthpiece 52 is urged downward. Further, the mouthpiece 52 is penetrated by a liquid passage 59 extending in the axial direction thereof. A first flow adjusting orifice 60 is formed at the lower end opening portion of the liquid passage 59.

The suction injection mouthpiece 53 is constructed in the same manner as the air/liquid injection mouthpiece 52. The mouthpiece 53 includes a flange 61 formed on the outer periphery of its upper end portion, and a ring-member 62 and a seal member 63 fixed on the outer peripheral surface of its lower end portion. The ring-member 62 includes a support portion 62a substantially equal in diameter to the flange 20b of the suction cylinder 18 and a collar portion 62b larger in diameter than the support portion 62a. Further, the mouthpiece 53 is penetrated by a liquid passage 64 extending in the axial direction thereof, and a second flow adjusting orifice 65 larger in diameter than the first orifice 60 is formed at the lower end opening portion of the liquid passage 64. The mouthpiece 53 is urged downward by a compression spring 66 as a second urging member which is interposed between the support plate 50 and the member 62.

The first and second orifices 60 and 65 constitute adjusting means for adjusting the passage resistance of the liquid passages 59 and 64, thereby regulating the flow rate of the detergent solution injected into the air, liquid and suction channels.

A flange 67 is formed on the outer periphery of the upper end portion of the gas cylinder plug 54 so as to be located on the upper surface side of the support plate 50. A disk-shaped backup member 68 substantially equal in diameter to the flange 20c of the gas cylinder 19 is fixed to the lower end of the plug 54. The backup member 68 has a projection 69 for opening the valve mechanism 19a in the gas cylinder 19. A ring-shaped seal member 70 is fixed to the lower surface of the backup member 68 around the projection 69, abutting against the upper surface of the flange 20c of the gas cylinder 19 in a liquid-tight manner. The gas cylinder plug 54 is urged downward by a compression spring 71 as a third urging member which is interposed between the support plate 50 and the backup member 68. The urging force of the spring 71 is greater than that of a spring 19b of the valve mechanism 19a.

A box-shaped slider 72 is slidably supported by the support plate 50. The slider 72 includes a rectangular bottom plate 72a separately facing the lower surface of the support plate 50, a pair of parallel side plates 72b extending beyond the support frame 50 from the side edges of the bottom plate 72a, and a front plate 72c extending close to the lower surface of the support plate 50 from the front edge of the bottom plate 72a. The front plate 72c can engage a pair of screws 74 as stoppers on the support plate 50. The upper end portion of each side plate 72b is bent inward to form a bent portion 72d which is in contact with the upper surface of the support plate 50.

Figure 7:
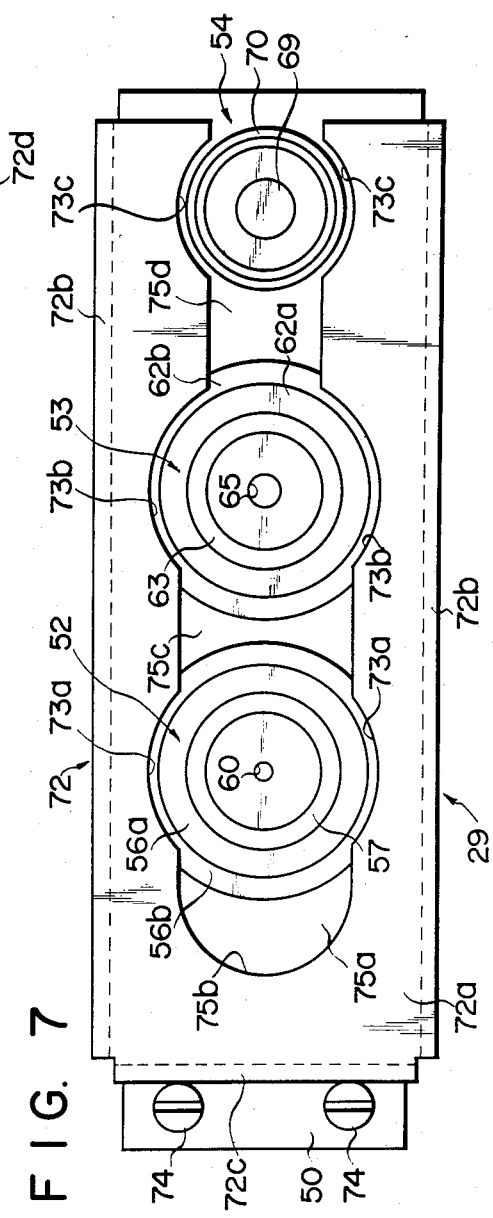
Figure 8:
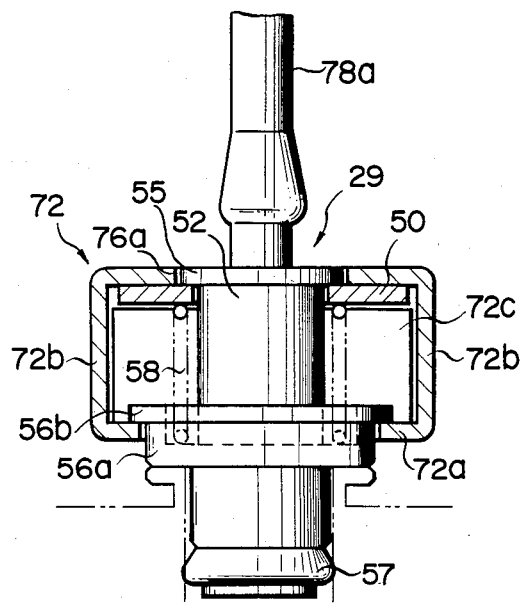

As shown in FIG. 7, the bottom plate 72a of the slider 72 is formed with three apertures 73a, 73b and 73c which are arranged side by side so that their centers are located on the longitudinal center line of the bottom plate 72a. The apertures 73a, 73b and 73c are designed so as to face the mouthpieces 52 and 53 and the gas cylinder plug 54, respectively, when the slider 72 is in its set position where the front plate 72c is in contact with the stoppers 74. The aperture 73a is a little larger in diameter than the support portion 56a of the ring-member 56 of the air/liquid injection mouthpiece 52 and narrower than the collar portion 56b. The aperture 73b is a little larger in diameter than the support portion 62a of the ring-member 62 of the suction injection mouthpiece 53 and narrower than the collar portion 62b. The aperture 73c is a little larger in diameter than the seal member 70 of the gas cylinder plug 54.

A slot 75a extends from the aperture 73a toward the front plate 72c of the slider 72 in the longitudinal direction of the bottom plate 72a. The width of the slot 75a is a little greater than the outside diameter of the air/liquid cylinder 17 and shorter than the diameter of the flange 20a. An extended end edge 75b of the slot 75a has the shape of an arc of a circle whose diameter is equal to the width of the slot 75a. Formed between the apertures 73a and 73b is a slot 75c which extends in the longitudinal direction of the bottom plate 72a and has a width a little longer than the outside diameter of the suction cylinder 18 and shorter than the diameter of the flange 20b. Formed between the apertures 73b and 73c is a slot 75d which extends in the longitudinal direction of the bottom plate 72a and has a width a little longer than the outside diameter of the gas cylinder 19 and shorter than the diameter of the flange 20c.

Figure 6:
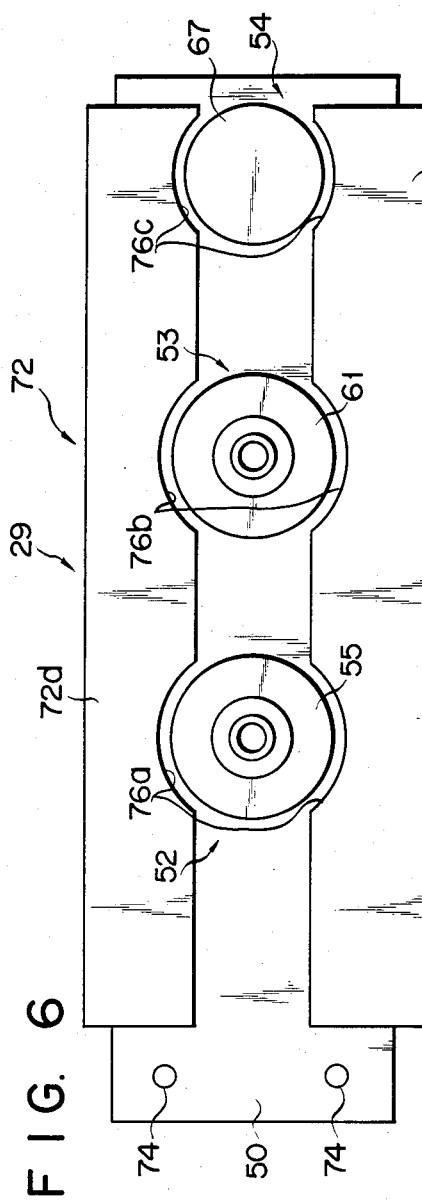

On the upper surface of the support plate 50, as shown in FIG. 6, the distance between the respective end edges of the two bent portions 72d of the slider 72 is greater than the diameters of the air/liquid injection mouthpiece 52, the suction injection mouthpiece 53, and the seal member 70 of the gas cylinder plug 54 and shorter than those of the flanges 55, 61 and 67. The end edge of each bent portion 72d is formed with an arcuate recess 76a shaped like an arc of a circle concentric with the air/liquid injection mouthpiece 52 and greater in diameter than the flange 55, an arcuate recess 76b shaped like an arc of a circle concentric with the suction injection mouthpiece 53 and greater in diameter than the flange 61, and an arcuate recess 76c shaped like an arc of a circle concentric with the gas cylinder plug 54 and greater in diameter than the flange 67.

The connecting unit 30 connecting the connector 29 and the liquid feeder 26 includes a Y-shaped branch pipe 77. One branch end 77a of the branch pipe 77 is connected to the air/liquid injection mouthpiece 52 by means of a branch tube 78a, while the other branch end 77b is connected to the suction injection mouthpiece 53 by means of a branch tube 78b. The remaining end 77c of the branch pipe 77 is connected to the outlet mouthpiece 36 of the simple-frame pump 27 by means of a main tube 79. Thus, the detergent solution from the liquid feeder 26 is fed to the air/liquid injection mouthpiece 52 and the suction injection mouthpiece 53 through the main tube 79, the branch pipe 77, and the branch tubes 78a and 78b.

There will now be described a method for cleaning the individual channels of the endoscope by the use of the cleaning apparatus constructed in the aforesaid manner.

First, the connector 29 of the cleaning apparatus is connected to the endoscope. In doing this, the slider 72 of the connector 29 is moved to the set position where the front plate 72c abuts aginst the stoppers 74, as shown in FIGS. 5 to 8. In this state, the apertures 73a, 73b and 73c in the bottom plate 72a of the slider 72 are located coaxial with the air/liquid injection mouthpiece 52, the suction injection mouthpiece 53, and the gas cylinder plug 54, respectively. The lower end portion of the mouthpiece 52 projects from the bottom plate 72a of the slider 72 through the aperture 73a, and the mouthpiece 52 is retained so that the collar portion 56b of the ring-member 56 is pressed against the inside of the bottom plate 72a by the spring 58. Likewise, the lower end portion of the mouthpiece 53 projects from the bottom plate 72a through the aperture 73b, and the mouthpiece 53 is retained so that the collar portion 62b of the ring-member 62 is pressed against the inside of the bottom plate 72a by the spring 66. Also, the lower end portion of the gas cylinder plug 54 projects from the bottom plate 72a through the aperture 73c, and the plug 54 is retained in a manner such that the flange 67 is pressed against the upper surface of the support plate 50 by the spring 71. In this state, the slider 72 would not be able to be slid to the right, since the end edges of the slots 75a, 75c and 75d in the bottom plate 72a of the slider 72 engage the support portions 56a and 62a of the ring-members 56 and 62 and the seal member 70 of the gas cylinder plug 54, respectively.

Subsequently, the lower end portions of the mouthpieces 52 and 53 are inserted into the air/liquid cylinder 17 and the suction cylinder 18, respectively, until the support portions 56a and 62a of the ring-members 56 and 62 abut against the flanges 20a and 20b of the cylinders 17 and 18, respectively. At the same time, the lower end portion of the gas cylinder plug 54 is inserted into the gas cylinder 19 until the seal member 70 abuts against the flange 20c of the gas cylinder 19. As a result, the projecting portion 69 of the plug 54 causes the valve mechanism 19a in the cylinder 19 to open.

Figure 11:
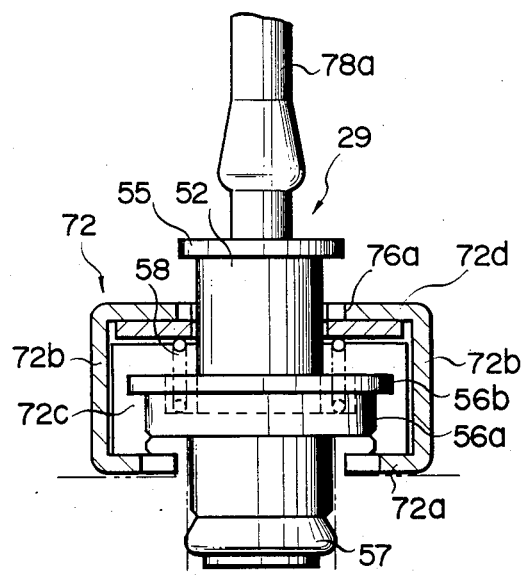
Figure 9:
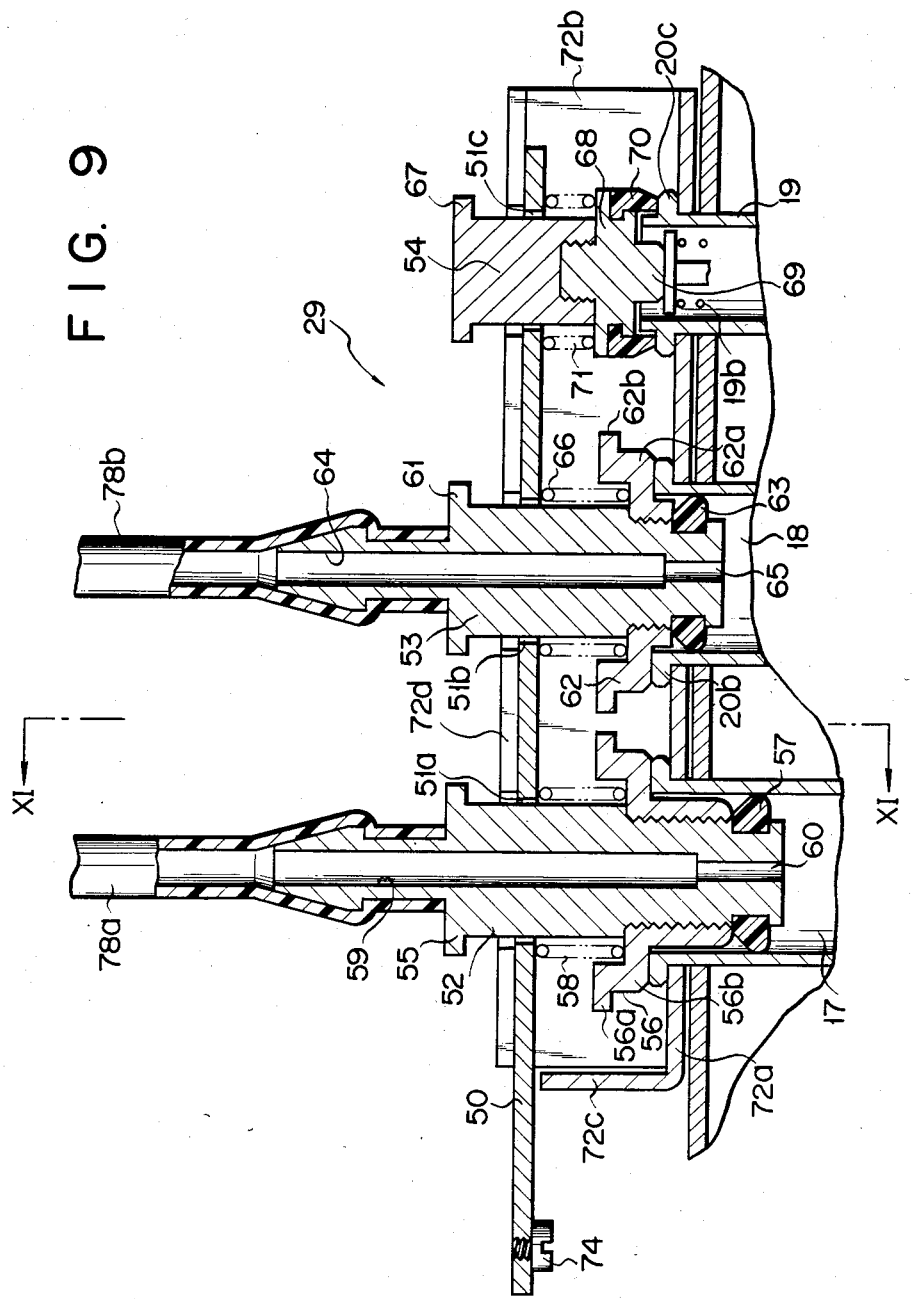
Figure 10:
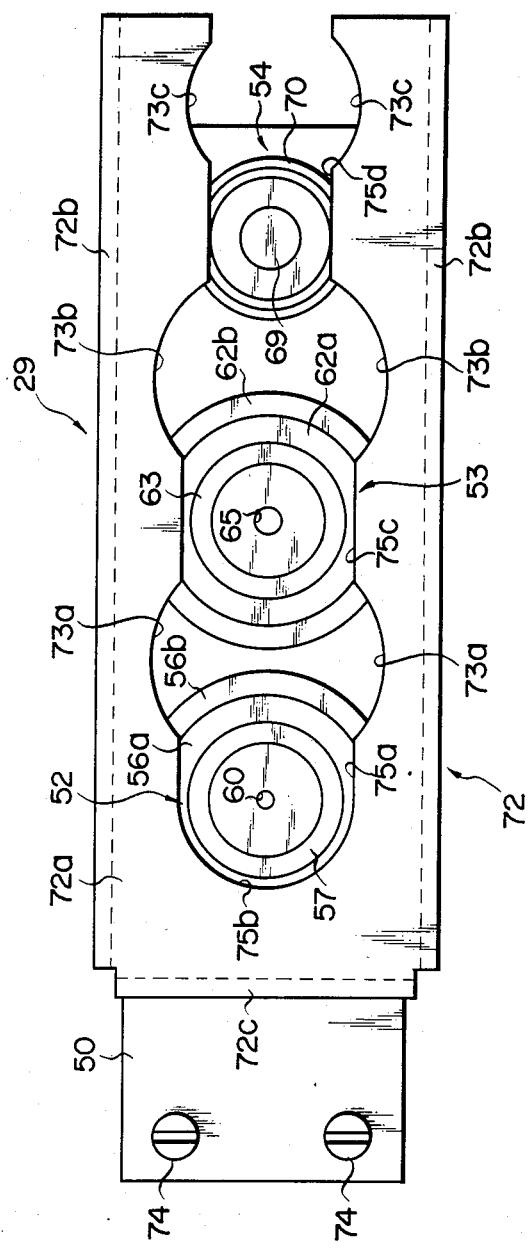

In this state, the slider 72, along with the support plate 50, is pressed down against the urging force of the springs 58, 66 and 71 until the bottom plate 72a of the slider 72 abuts against the outer surface of the operating section 2 of the endoscope. Further, the slider 72 is slid to the right to reach a hold position where the front end edge 75b of the slot 75a in the bottom plate 72a engages the outer peripheral surface of the upper end portion of the air/liquid cylinder 17, as shown in FIGS. 9 to 11. In the hold position, the end edge portions of the slot 75a are located between the lower surface of the flange 20a of the air/liquid cylinder 17 and the outer surface of the operating section 2 of the endoscope. Likewise, the end edge portions of the slot 75c are located between the lower surface of the flange 20b of the suction cylinder 18 and the outer surface of the operating section 2, and those of the slot 75d between the lower surface of the flange 20c of the gas cylinder 19 and the outer surface of the operating section 2.

In this state, if the press on the slider 72 is removed, the support plate 50 and the slider 72 are moved slightly upward by the springs 58, 66 and 71. As a result, the end edge portions of the slots 75a, 75c and 75d are pressed against the lower surfaces of the flanges 20a, 20b and 20c of the cylinders 17, 18 and 19, respectively. Thus, the flange 20a of the air/liquid cylinder 17 is held between the end edge portions of the slot 75a and the ring-member 56 of the mouthpiece 52, and the flange 20b of the suction cylinder 18 between the end edge portions of the slot 75c and the ring-member 62 of the mouthpiece 53. Also, the flange 20c of the gas cylinder 19 is held between the end edge portions of the slot 75d and the seal member 70 of the gas cylinder plug 54. Consequently, the connector 29 is locked to the position shown in FIG. 9, when the connection of the connector 29 is completed.

Thereafter, the piston 46 of the operating member 46 is repeatedly pushed and pulled to feed the detergent solution into the individual channels of the endoscope through the connecting unit 30 and the connector 29. When the piston 46 is pulled, a negative pressure is produced in the liquid passage 31 of the pump 27, so that the check valves 40a and 40b are closed and opened, respectively. As a result, the detergent solution in the tank 49 is sucked into the liquid passage 31 through the filter 48 and the suction tube 47. When the piston 46 is then pushed in, a positive pressure is produced in the liquid passage 31, so that the check valves 40a and 40b are opened and closed, respectively. As a result, the detergent solution sucked into the liquid passage 31 is fed into the main tube 79 of the connecting unit 30 through the outlet mouthpiece 36. Thus, the detergent solution in the tank 49 is intermittently supplied to the main tube 79 by repeatedly reciprocating the piston 46.

Part of the detergent solution fed into the main tube 79 flows into the air/liquid cylinder 17 through the branch pipe 77, the branch tube 78a, and the liquid passage 59 of the air/liquid injection mouthpiece 52. The remaining part of the detergent solution flows into the suction cylinder 18 through the branch pipe 77, the branch tube 78b, and the liquid passage 64 of the suction injection mouthpiece 53. The detergent solution introduced into the air/liquid cylinder 17 flows through the air channel 5 and the liquid channel 6, and is discharged through the distal end of the insertion section 3 and the mouthpieces 13 and 14 of the connector 4a of the universal cord 4. Part of the detergent solution introduced into the air channel 5 passes through the gas channel 8 and the gas cylinder 19, and is discharged through the mouthpiece 16 of the connector 4a. The detergent solution fed into the suction cylinder 18 passes through the suction channel 7, and is discharged through the distal end of the insertion section 3, the forceps port 21, and the mouthpiece 15 of the connector 4a. Thus, the cylinders 17, 18 and 19 and the channels 5, 6, 7 and 8 are washed and cleaned.

The amounts of detergent solution supplied to the air/liquid cylinder 17 and the suction cylinder 18 are adjusted by means of the first and second orifices 60 and 65 as the adjusting means in the air/liquid injection mouthpiece 52 and the suction injection mouthpiece 53. The air and liquid channels 5 and 6 are smaller in diameter than the suction channel 7, and the first orifice 60 communicating with the air and liquid channels is narrower than the second orifice 65 communicating with the suction channel 7, correspondingly. Therefore, the passage resistance of the first orifice 60 is greater than that of the second orifice 65, so that the air/liquid cylinder 17 is supplied with less detergent solution than the suction cylinder 18 is.

In removing the connector 29 from the endoscope after the cleaning of the endoscope is finished, the slider 72 is moved to the set position shown in FIG. 5. As a result, the slider 72 and the support plate 50 are raised to the position of FIG. 5 by the springs 58, 66 and 71. Thereafter, the connector 29 is disconnected from the endoscope by drawing out the lower end portions of the mouthpieces 52 and 53 and the gas cylinder plug 54 from the air/liquid cylinder 17, the suction cylinder 18, and the gas cylinder 19, respectively.

Constructed in this manner, the cleaning apparatus provides the following functions or effects.

The connector 29 of the cleaning apparatus can be easily and securely connected to or removed from the endoscope. Namely, the connector 29 can be connected to the endoscope by only pushing the slider 72 to slide the same after inserting the lower end portions of the mouthpieces 52 and 53 and the gas cylinder plug 54 into the air/liquid cylinder 17, the suction cylinder 18, and the gas cylinder 19, respectively. When the connector 29 is connected to the endoscope, the flanges 20a, 20b and 20c of the individual cylinders are held between the slider 72 and the mouthpieces 52 and 53 and the gas cylinder plug 54 with the aid of the urging force of the spring 58, 66 and 71. Even when it is subjected to a force in a direction to remove it from the cylinders of the endoscope, therefore, the connector 29 can securely be retained as it is connected to the endoscope. In removing the connector 29, moreover, the slider 72 and the support plate 50 can be returned to their initial position by the urging force of the springs 58, 66 and 71 if the slider 72 is simply slid. Thus, the connector 29 can easily be disconnected from the endoscope by only drawing out the mouthpieces 52 and 53 and the gas cylinder plug 54 from their corresponding cylinders after sliding the slider 72.

Further, the cleaning apparatus is provided with the first and second orifices 60 and 65 as the flow adjusting means, so that it is possible to feed a relatively small amount of detergent solution to the air, liquid, and gas channels which have a small capacity, and a larger amount of detergent solution to the suction channel whose capacity is greater. Thus, it is possible to full supply a large-capacity channel with the detergent solution. Even with use of the simple-frame pump as the liquid feeder, therefore, the channels of the endoscope can satisfactorily be cleaned by a relatively few processes of liquid feeding operation.

Figure 12:
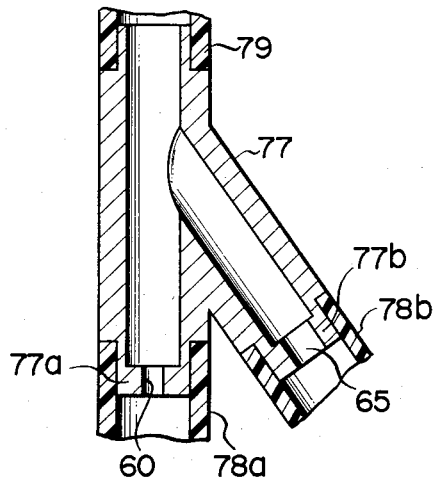

Instead of providing the mouthpieces 52 and 53 of the connector 29 with the orifices as the flow adjusting means, in the first embodiment described above, orifices may be formed in the branch pipe 77 of the connecting unit 30, as shown in FIG. 12. In this case, the first orifice 60 is formed in that end opening 77a of the branch pipe 77 which is connected to the air/liquid injection mouthpiece 52 by means of the branch tube 78a, while the second orifice 65 larger in diameter than the first orifice 60 is formed in the end opening 77b connected to the suction injection mouthpiece 53 by means of the branch tube 78b.

The above-mentioned modification may provide the same functions or effects of the first embodiment.

Figure 13:
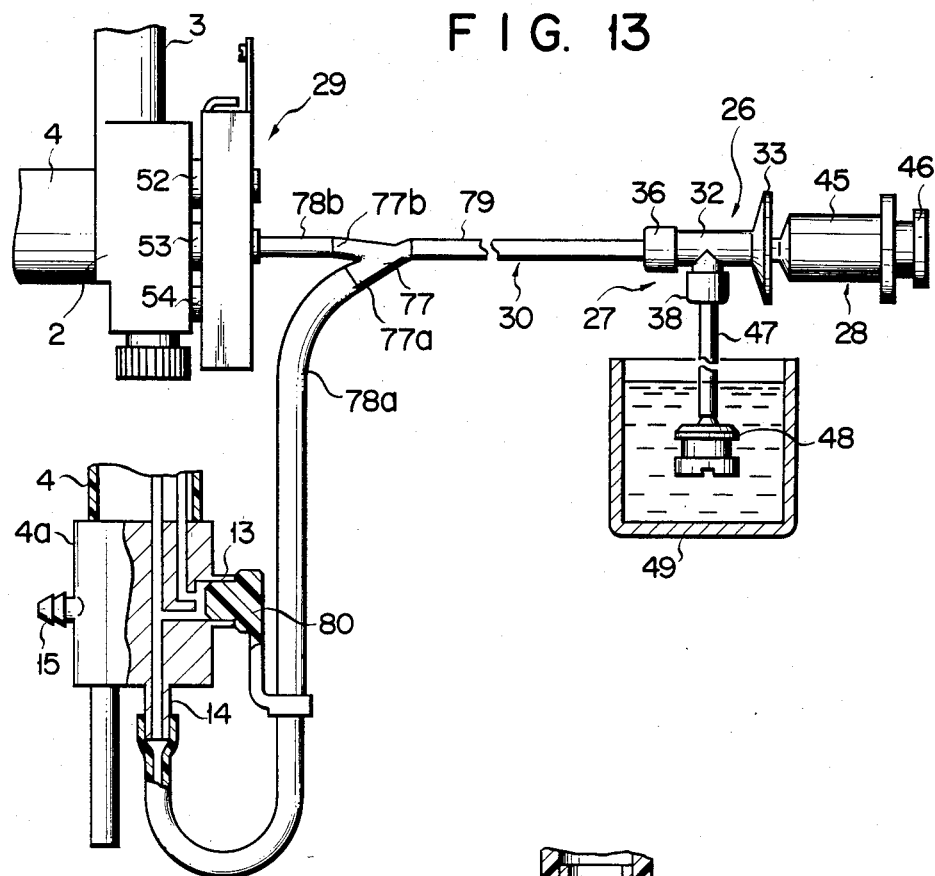

FIG. 13 shows a specific example of the cleaning apparatus using the branch pipe 77 shown in FIG. 12. According to this example, the branch tube 78a of the connecting unit 30 is connected to the air mouthpiece 14 formed on the connector 4a of the endoscope instead of being connected to the air/liquid injection mouthpiece 52. In this case, the liquid passage 59 (FIG. 5) of the air/liquid injection mouthpiece 52 is blocked up, and the liquid mouthpiece 13 of the connector 4a is closed by an elastic plug 80.

Also in this specific example, the channels and cylinders of the endoscope can satisfactorily be cleaned.

FIGS. 14 to 17 show a second embodiment of the present invention. The fundamental arrangement of this embodiment is the same as that of the first embodiment, except for the use of a motor-operated pump 81 for the liquid feeder 26. In the description to follow, therefore, like reference numerals are used to designate like portions as included in the first embodiment, and only the difference of the second embodiment from the first embodiment will be described.

As shown in FIG. 14, the suction tube 47 is connected to the suction side of the motor-operated pump 81, and the main tube 79 to the discharge side. The lower end portions of the air/liquid injection mouthpiece 52 and the suction injection mouthpiece 53 of the connector 29 are not adapted to be inserted into the air/liquid cylinder 17 or the suction cylinder 18 of the endoscope. Namely, the ring-member 56 is fixed to the bottom end of the mouthpiece 52. The support portion 56a of the member 56 has a flat lower surface, which is formed with a ring-shaped fitting portion 56c. The inside diameter of the fitting portion 56c is a little greater than the diameter of the flange 20a of the cylinder 17, and its height is equal to the thickness of the flange 20a. The seal member 57 is embedded in the lower surface of the support portion 56a and can engage the upper surface of the flange 20a. Likewise, the ring-member 62 is fixed to the bottom end of the mouthpiece 53. The support portion 62a of the member 62 has a flat lower surface, which is formed with a ring-shaped fitting portion 62c. The inside diameter of the fitting portion 62c is a little greater than the diameter of the flange 20b, and its height is equal to the thickness of the flange 20b. The seal member 63 is embedded in the lower surface of the support portion 62a and can engage the upper surface of the flange 20b.

In contrast with the case of the first embodiment in which the simple-frame pump is used as the liquid feeder, the first orifice 60 formed in the mouthpiece 52, according to the second embodiment, is larger in diameter than the second orifice 65 in the mouthpiece 53. This is because the use of the motor-operated pump 81 for continuous feed of the detergent solution would cause the detergent solution to be prevented from smoothly flowing through the channels of the endoscope by the difference in flow resistance between the channels. If the first orifice 60 communicating with the air, liquid, and gas channels which have smaller diameters or higher flow resistance is made wider than the second orifice 65 communicating with the suction channel which has lower flow resistance, however, the detergent solution can be fed under a uniform pressure into the channels and smoothly flow through the same substantially at a time.

Figure 16:
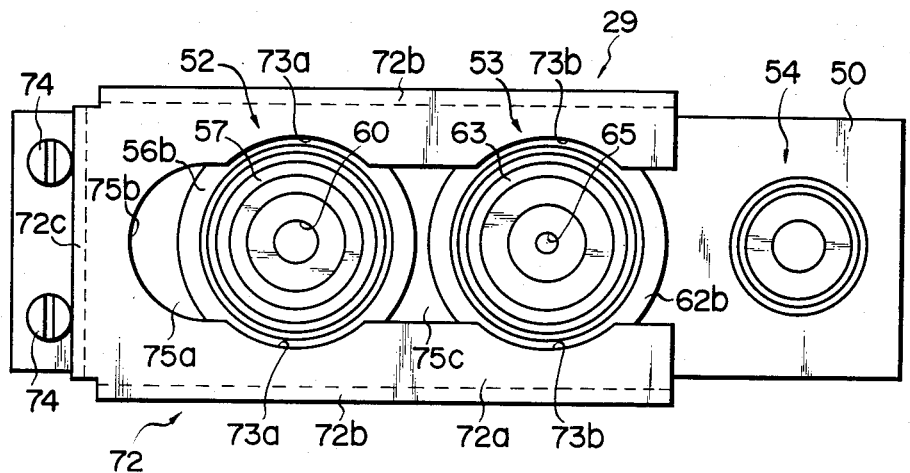

The gas cylinder plug 54 is fixed to the support plate 50 by means of a nut 82. As shown in FIGS. 15 and 16, moreover, the slider 72 is cut at its rear end portion which should otherwise engage the gas cylinder 19 and the gas cylinder plug 54.

Figure 17:
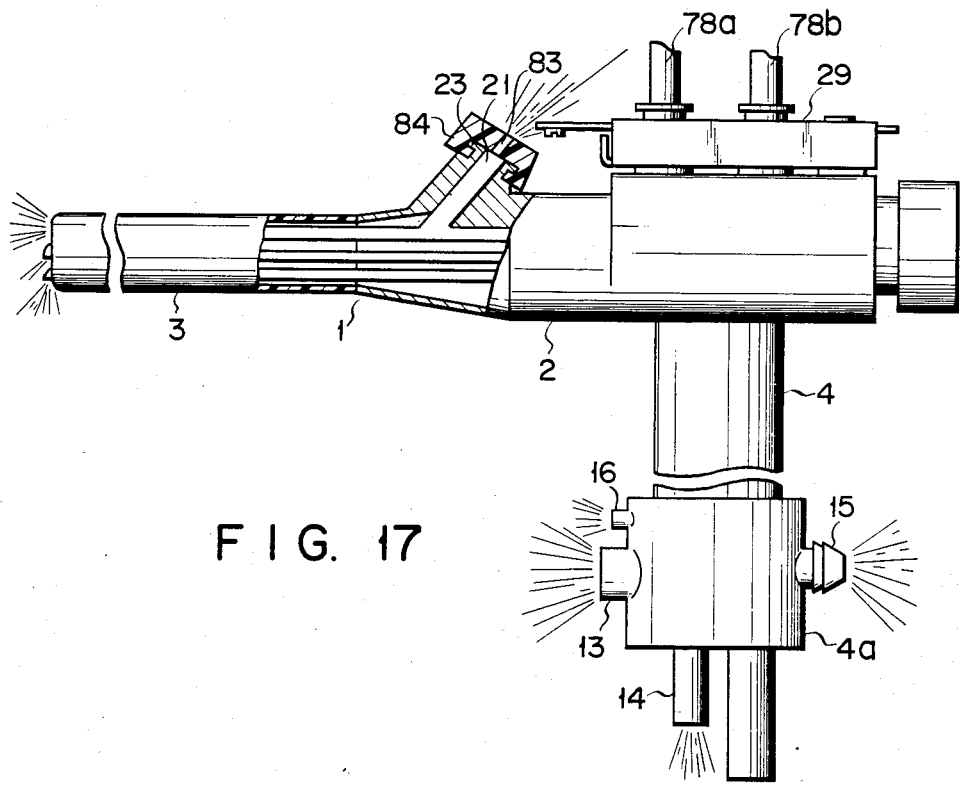

As shown in FIG. 17, the forceps mouthpiece 21 of the endoscope is fitted with an adjusting stopper 84 having a third orifice 83.

According to the second embodiment constructed in this manner, the detergent solution may be continuously fed into the channels of the endoscope by the motor-pump 81, thereby fully cleaning the channels. Since the first to third orifices 60, 65 and 83 serve to adjust the flow resistance of the channels, the detergent solution can smoothly flow through the channels. Moreover, the mouthpieces 52 and 53 of the connector 29 are not provided with any insertion portions to be inserted into the air/liquid cylinder 17 or the suction cylinder 18, so that the whole regions inside the cylinders 17 and 18 can be cleaned. Since the gas cylinder plug 54 is fixed to the support plate 50, the connector 29 may enjoy a simple construction.

The adjusting stopper 84 may be fitted on the suction mouthpiece 15 of the connector 4a of the endoscope instead of the forceps mouthpiece 21. In the second embodiment, furthermore, the cleaning apparatus is provided with both the second orifice 65 in the mouthpiece 53 and the third orifice 83 in the adjusting stopper 84. However, use of only one of these orifices may provide the same functions or effects.

Figure 18:
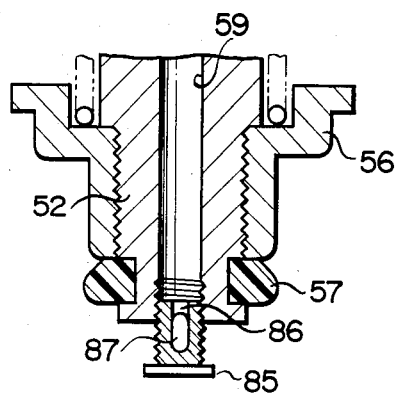
FIG. 18 is a sectional view showing a modified example of flow adjusting means.

Although the flow adjusting means used in the first and second embodiments is a constant-type orifice, it may alternatively be formed of a variable-type orifice, as shown in FIG. 18. The variable orifice includes, for example, a screw-shaped member 85 which is screwed in the lower end opening of the liquid passage 59 formed in the air/liquid injection mouthpiece 52. The member 85 is formed with a bottomed passage 86 extending in its axial direction and an orifice forming hole 87 penetrating the member 85 and intersecting the passage 86. The flow resistance of the liquid passage 59 can be varied by adjusting the depth of screwing of the member 85 to change the opening area of the orifice forming hole 87.

Use of the variable orifice allows the single connector 29 to be combined with either a simple-frame pump or motor-operated pump.

Figure 19:
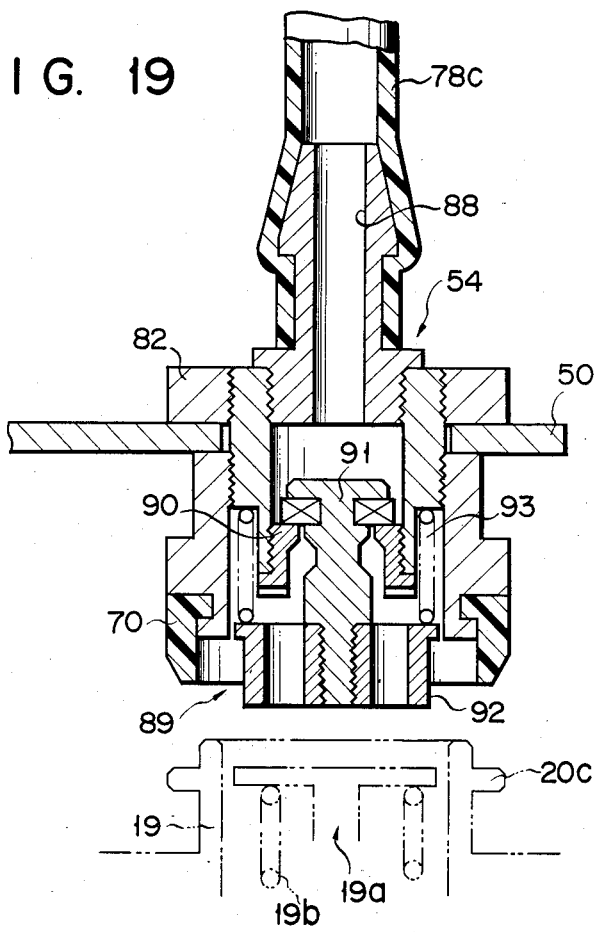
FIG. 19 is a sectional view showing a modified example of a gas cylinder plug.

In the first and second embodiments, the gas cylinder plug 54 may be constructed as shown in FIG. 19. In the modified example shown in FIG. 19, the gas cylinder plug 54 is fixed to the support plate 50 by means of the nut 82, and has a liquid passage 88 penetrating the plug 54 along its axis. A valve mechanism 89 is set in the liquid passage 88. The valve mechanism 89 includes a ring-shaped valve seat 90 fixed to the inner peripheral surface of the liquid passage 88, a valve 91 movable in the axial direction of the liquid passage 88, a press cylinder 92 fixed to the valve and adapted to open the valve mechanism 19a in the gas cylinder 19, and a spring 93 for urging the valve and the press cylinder 92 to project from the bottom opening of the liquid passage 88. The liquid passage 88 is connected to the liquid feeder by means of a tube 78c.

When the gas cylinder plug 54 with the above described construction is connected to the gas cylinder 19 of the endoscope, the press cylinder 92 opens the valve mechanism 19a in the gas cylinder 19, and the valve 91 rises to open the valve mechanism 89. Thereupon, the detergent solution may be fed from the liquid feeder into the gas cylinder 19 and the gas channel through the tube 78c and the liquid passage 88. Thus, the channels of the endoscope can be cleaned more securely. Unless the press cylinder 92 is pressed, the valve mechanism 89 is closed, so that the detergent solution is prevented from flowing out through the liquid passage 88. Thus, the connector 29 with the aforementioned gas cylinder plug 54 may be applied also to an endoscope without the gas cylinder 19.

Figure 20:
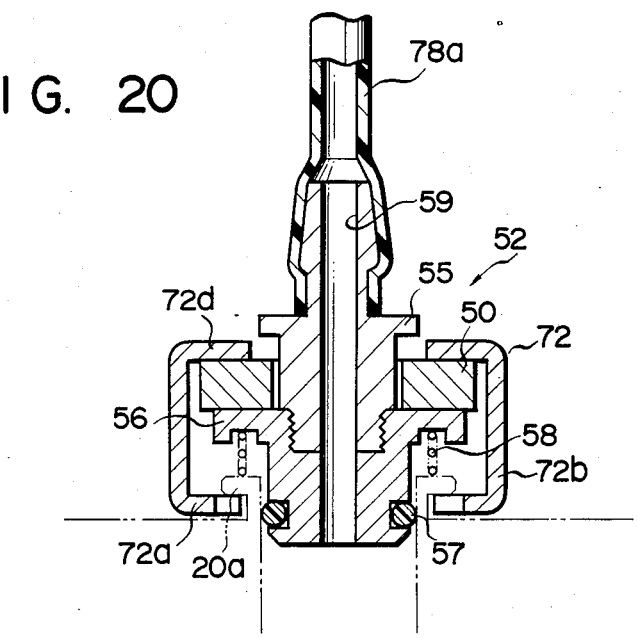
FIGS. 20 and 21 are sectional views showing different modified examples of the connector.

In the first and second embodiments, the first urging member 58 of the connector 29 is interposed between the support plate 50 and the ring-member of the mouthpiece. Alternatively, however, it may be fixed to the lower surface of the ring-member 56 so as to directly abut against the flange 20a of the cylinder 18, as shown in FIG. 20, for example. In this case, the flange 20a is held between the bottom plate 72a of the slider 72 and the urging member 58.

Figure 21:
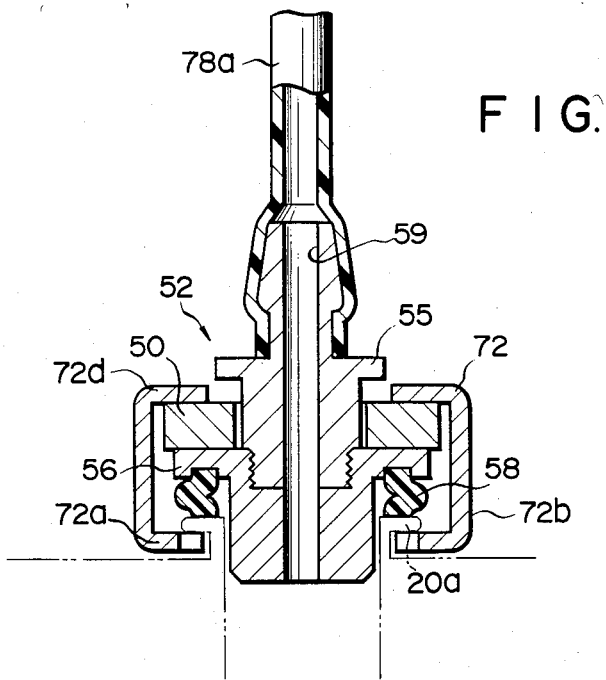

As shown in FIG. 21, moreover, an elastic material such as rubber may be used in place of the spring as the first urging member. In this case, the first urging member may serve also as a seal member, permitting a reduction in the number of components used in the apparatus and simpler construction thereof.

It is to be understood that the modified examples shown in FIGS. 20 and 21 may be applied also to the second urging member 66.

Figure 22:
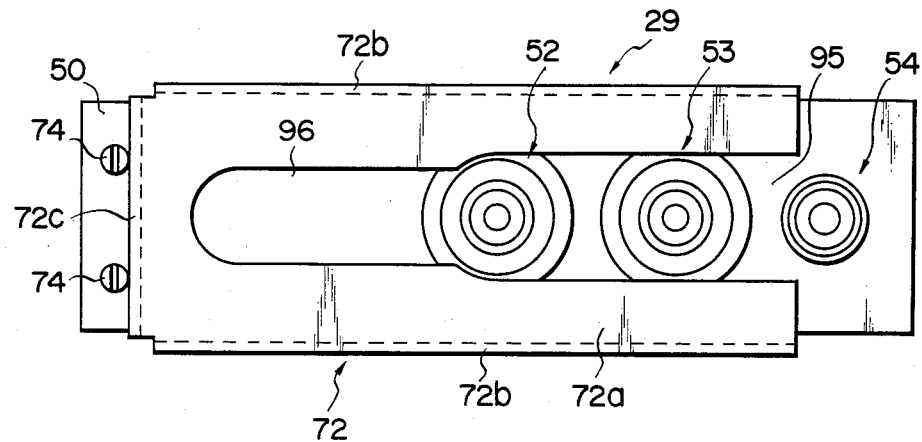
FIG. 22 is a top view showing a modified example of a slider.

The slider 72 of the connector 29 may be constructed as shown in FIG. 22. In stead of boring the apertures through the bottom plate 72a, according to this modified example, first and second slots 95 and 96 are continuously formed in the bottom plate. The width of the first slot 95 is longer than the diameter of the support portion of each ring-member of the mouthpiece 52 or 53 and shorter than the diameter of the collar portion, while that of the second slot 96 is a little longer than the outside diameter of each cylinder and shorter than the diameter of the flange of the cylinder.

In this example, although the slider 72 requires a longer stroke, it can be worked more easily.

Figure 23:
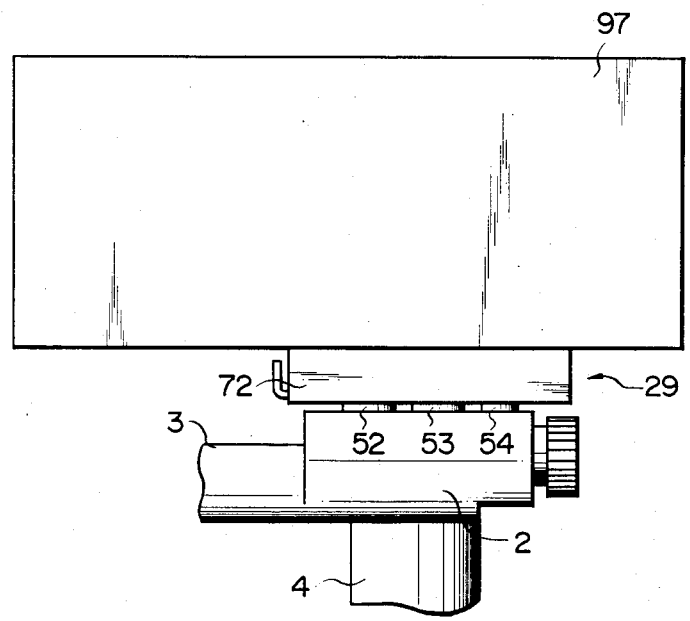
FIG. 23 is a side view of a cleaning apparatus according to a third embodiment of the invention.

As shown in FIG. 23, moreover, the connector 29 may be formed integrally with a housing 97 which contains therein the liquid feeder, connecting unit and the like.

In the first and second embodiments, the engaging portion of each cylinder consists of the flange 20a (or 20b or 20c) which covers the whole peripheral surface of the upper end portion of the cylinder, as shown in FIGS. 24A and 24B. Alternatively, however, the engaging portion may include a pair of arcuate flanges 98 which are formed on the outer peripheral surface of the cylinder, facing each other, as shown in FIGS. 25A and 25B. Further, screws 99 may be used in place of the flanges for the engaging portion, as shown in FIGS. 26A and 26B. As shown in FIGS. 27A and 27B, furthermore, two parallel grooves 100 formed on the outer peripheral surface of the upper end portion of the cylinder may be used for the engaging portion.

What is claimed is:

1. A cleaning apparatus for cleaning channels of an endoscope which comprises an operating section, an insertion section extending from the operating section, a universal cord extending from the operating section, an air channel, a liquid channel and a suction channel extending inside the endoscope, an air/liquid cylinder provided at the operating section and communicating with the air channel and the liquid channel, and a suction cylinder provided at the operating section and communicating with the suction channel, said air/liquid cylinder and said suction cylinder each including an open end portion projecting from the operating section and an engaging portion formed on the open end portion, said apparatus comprising:

liquid feeding means for feeding a detergent solution;
a connector detachably connected to the air/liquid cylinder and the suction cylinder; and
connecting means for connecting the liquid feeding means and the connector to deliver the detergent solution fed from the liquid feeding means into the channels of the endoscope through the connector, said connector including
a support body,
an air/liquid mouthpiece movably supported by the support body and connected to the open end portion of the air/liquid cylinder in a liquid-tight manner, said air/liquid mouthpiece having a liquid passage communicating with the inside of the air/liquid cylinder and the connecting means and a retaining portion engaging the engaging portion of the air/liquid cylinder, a suction mouthpiece movably supported by the support body and connected to the open end portion of the suction cylinder in a liquid-tight manner, said suction mouthpiece having a liquid passage communicating with the inside of the suction cylinder and the connecting means and a retaining portion engaging the engaging portion of the suction cylinder, a slider slidably supported by the support body and having a first holding portion adapted to engage the engaging portion of the air/liquid cylinder and a second holding portion adapted to engage the engaging portion of the suction cylinder, said slider being movable between a first position where the first and second holding portions of the slider are disengaged from the engaging portions of the cylinders, and a second position where the first holding portion engages the engaging portion of the air/liquid cylinder to hold the engaging portion of the air/liquid cylinder between the first holding portion and the retaining portion of the air/liquid mouthpiece, and where the second holding portion engages the engaging portion of the suction cylinder to hold the engaging portion of the suction cylinder between the second holding portion and the retaining portion of the suction mouthpiece, and urging means for urging the first and second holding portions toward the respective retaining portions of the air/liquid mouthpiece and the suction mouthpiece when the slider is moved to the second position.

2. The cleaning apparatus according to claim 1, wherein said support body includes a support plate having first and second apertures facing the open ends of the air/liquid cylinder and the suction cylinder, respectively, said air/liquid mouthpiece includes a substantially cylindrical body passed through the first aperture and a flange formed on one end portion of the body and located on one side of the support plate, said retaining portion of the air/liquid mouthpiece having a ring-member fixed on the outer peripheral surface of the other end portion of the body and located on the other side of the support plate, and said suction mouthpiece includes a substantially cylindrical body passed through the second aperture and a flange formed on one end portion of the body and located on the one side of the support plate, said retaining portion of the suction mouthpiece having a ring-member fixed on the outer peripheral surface of the other end portion of the body and located on the other side of the support plate.

3. The cleaning apparatus according to claim 2, wherein said urging means includes a first urging member disposed between the support plate and the ring-member of the air/liquid mouthpiece so as to surround the air/liquid mouthpiece, and a second urging member disposed between the support plate and the ring-member of the suction mouthpiece so as to surround the suction mouthpiece.

4. The cleaning apparatus according to claim 3, wherein said ring-member of the air/liquid mouthpiece includes an annular support portion abutting against the open end edge of the air/liquid cylinder and a collar portion larger in diameter than the support portion and located on the support plate side of the support portion, said ring-member of the suction mouthpiece includes an annular support portion abutting against the open end edge of the suction cylinder and a collar portion larger in diameter than the support portion and located on the support plate side of the support portion, and said slider includes a first retaining portion adapted to engage the collar portion of the air/liquid mouthpiece to restrain the movement of the air/liquid mouthpiece when the slider is in the first position, and a second retaining portion adapted to engage the collar portion of the suction mouthpiece to restrain the movement of the suction mouthpiece when the slider is in the first position.

5. The cleaning apparatus according to claim 4, wherein said slider includes a bottom plate facing the support plate at a predetermined distance therefrom and movable parallel to the support plate; a first through hole formed in the bottom plate to face the first aperture when the slider is in the first position, the diameter of said first through hole being greater than that of the support portion of the ring-member of the air/liquid mouthpiece and smaller than that of the collar portion and the peripheral edge portion of the first through hole constituting said first retaining portion; a second through hole formed in the bottom plate to face the second aperture when the slider is in the first position, the diameter of said second through hole being greater than that of the support portion of the ring-member of the suction mouthpiece and the peripheral edge portion of the second through hole constituting said second retaining portion; a first slot formed in the bottom plate and extending along the moving direction of the slider from the first through hole, the width of said first slot being longer than the outside diameter of the air/liquid cylinder and shorter than the diametrical length of the engaging portion of the air/liquid cylinder and the end edge portions of the first slot constituting said first holding portion; and a second slot formed in the bottom plate and extending along the moving direction of the slider between the first and second through holes, the width of said second slot being longer than the outside diameter of the suction cylinder and shorter than the diametrical length of the engaging portion of the suction cylinder and the end edge portions of the second slot constituting said second holding portion.

6. The cleaning apparatus according to claim 4, wherein said air/liquid mouthpiece includes an insertion portion adapted to be inserted into the air/liquid cylinder and a ring-shaped seal member fixed on the outer peripheral surface of the insertion portion and adapted to be in liquid-tight contact with the inner peripheral surface of the air/liquid cylinder, and said suction mouthpiece includes an insertion portion adapted to be inserted into the suction cylinder and a ring-shaped seal member fixed on the outer peripheral surface of the insertion portion and adapted to be in liquid-tight contact with the inner peripheral surface of the suction cylinder.

7. The cleaning apparatus according to claim 4, wherein said support portion of the ring-member of the air/liquid mouthpiece includes an end face abutting against the open end edge of the air/liquid cylinder to close the open end of the air/liquid cylinder and a ring-shaped seal member fixed to the end face and adapted to be in liquid-tight contact with the open end edge of the air/liquid cylinder, and said support portion of the ring-member of the suction mouthpiece includes an end face abutting against the open end edge of the suction cylinder to close the open end of the suction cylinder and a ring-shaped seal member fixed to the end face and adapted to be in liquid-tight contact with the open end edge of the suction cylinder.

8. The cleaning apparatus according to claim 2, wherein said urging means includes a first compression coil spring fixed to the ring-member of the air/liquid mouthpiece and abutting against the open end edge of the air/liquid cylinder and a second compression coil spring fixed to the ring-member of the suction mouthpiece and abutting against the open end edge of the suction cylinder, said air/liquid mouthpiece includes an insertion portion adapted to be inserted into the air/liquid cylinder and a ring-shaped seal member fixed on the outer peripheral surface of the insertion portion and adapted to be in liquid-tight contact with the inner peripheral surface of the air/liquid cylinder, and said suction mouthpiece includes an insertion portion adapted to be inserted into the suction cylinder and a ring-shaped seal member fixed on the outer peripheral surface of the insertion portion and adapted to be in liquid-tight contact with the inner peripheral surface of the suction cylinder.

9. The cleaning apparatus according to claim 2, wherein said urging means includes a first ring-shaped urging member formed of an elastic material, said first urging member being fixed to the ring-member of the air/liquid mouthpiece and in liquid-tight contact with the open end edge of the air/liquid cylinder, and a second ring-shaped urging member formed of an elastic material, said second urging member being fixed to the ring-member of the suction mouthpiece and in liquid-tight contact with the open end edge of the suction cylinder.

10. The cleaning apparatus according to claim 1, which further comprises adjusting means for adjusting the amount of detergent solution fed into the individual channels of the endoscope.

11. The cleaning apparatus according to claim 10, wherein said liquid feeding means includes a simple-frame pump for intermittently feeding the detergent solution.

12. The cleaning apparatus according to claim 11, wherein said adjusting means includes a first orifice formed in the liquid passage of the air/liquid mouthpiece and a second orifice formed in the liquid passage of the suction mouthpiece and larger in diameter than the first orifice.

13. The cleaning apparatus according to claim 11, wherein said connecting means includes a branch pipe having a main port portion and first and second branch port portions communicating with the main port portion, a main tube connecting the main port portion and the liquid feeding means, a first branch tube connecting the first branch port portion and the air/liquid mouthpiece, and a second branch tube connecting the second branch port portion and the suction mouthpiece, and said adjusting means includes a first orifice formed in the first branch port portion and a second orifice formed in the second branch port portion and larger in diameter than the first orifice.

14. The cleaning apparatus according to claim 10, wherein said liquid feeding means includes a motor-operated pump for continuously feeding the detergent agent.

15. The cleaning apparatus according to claim 14, wherein said adjusting means includes a first orifice formed in the liquid passage of the air/liquid mouthpiece and a second orifice formed in the liquid passage of the suction mouthpiece and smaller in diameter than the first orifice.

16. The cleaning apparatus according to claim 14, wherein said connecting means includes a branch pipe having a main port portion and first and second branch port portions communicating with the main port portion, a main tube connecting the main port portion and the liquid feeding means, a first branch tube connecting the first branch port portion and the air/liquid mouthpiece, and a second branch tube connecting the second branch port portion and the suction mouthpiece, and said adjusting means includes a first orifice formed in the first branch port portion and a second orifice formed in the second branch port portion and smaller in diameter than the first orifice.

17. The cleaning apparatus according to claim 16, wherein said endoscope includes a forceps mouthpiece formed on the operating section and a forceps channel extending from the forceps mouthpiece and communicating with the suction channel, and said adjusting means includes a stopper having a third orifice and fitted on the forceps mouthpiece.

18. The cleaning apparatus according to claim 1, wherein said endoscope includes a gas channel extending inside the endoscope and communicating with the air channel and a gas cylinder provided at the operating section and communicating with the gas channel, said gas cylinder including an open end portion projecting from the operating section and an engaging portion formed on the open end portion, said cleaning apparatus further comprising a gas cylinder plug adapted to be connected to the open end portion of the gas cylinder in a liquid-tight manner.

19. The cleaning apparatus according to claim 18, wherein said gas cylinder plug includes a liquid passage communicating with the inside of the gas cylinder and the connecting means.

* * * * *